(12) United States Patent
Schierbaum et al.

(10) Patent No.: US 9,921,175 B2
(45) Date of Patent: Mar. 20, 2018

(54) SENSOR AND METHOD FOR MANUFACTURING A SENSOR

(71) Applicant: HEINRICH-HEINE UNIVERSITÄT DÜSSELDORF, Düsseldorf (DE)

(72) Inventors: Klaus Schierbaum, Krefeld (DE); Mhamed El Achhab, Düsseldorf (DE); Christiane Schüle, Düsseldorf (DE)

(73) Assignee: HEINRICH-HEINE UNIVERSITÄT DÜSSELDORF, Düsseldorf (DE)

( * ) Notice: Subject to any disclaimer, the term of this patent is extended or adjusted under 35 U.S.C. 154(b) by 481 days.

(21) Appl. No.: 14/351,097

(22) PCT Filed: Oct. 10, 2012

(86) PCT No.: PCT/EP2012/070066
§ 371 (c)(1),
(2) Date: Apr. 10, 2014

(87) PCT Pub. No.: WO2013/053762
PCT Pub. Date: Apr. 18, 2013

(65) Prior Publication Data
US 2014/0291160 A1    Oct. 2, 2014

(30) Foreign Application Priority Data

Oct. 14, 2011   (DE) .................. 10 2011 054 501

(51) Int. Cl.
*G01N 27/26*    (2006.01)
*C25D 7/00*    (2006.01)
*G01N 27/12*    (2006.01)

(52) U.S. Cl.
CPC ............ *G01N 27/127* (2013.01); *C25D 7/00* (2013.01); *G01N 27/125* (2013.01); *G01N 27/26* (2013.01)

(58) Field of Classification Search
None
See application file for complete search history.

(56) References Cited

U.S. PATENT DOCUMENTS 4,217,623 A * 8/1980 Nishino ............... G01N 27/225
361/280
4,433,319 A * 2/1984 Luder .................. G01N 27/121
338/34

(Continued)

FOREIGN PATENT DOCUMENTS

AT        007429 U1   3/2005
DE      10260857 A1   7/2004

(Continued)

OTHER PUBLICATIONS

Zdansky (Nanoscale Research Letters Aug. 2010, 6:490).*

(Continued)

*Primary Examiner* — Luan Van
*Assistant Examiner* — Steven E Rosenwald
(74) *Attorney, Agent, or Firm* — Davidson, Davidson & Kappel, LLC (57) ABSTRACT

The present invention refers to a sensor (10) having a layer arrangement (12), wherein the layer arrangement (12) comprises at least a base layer (14), a middle layer (16) and an outer layer (18), wherein the middle layer (16) is arranged at least partly upon and in contact with the base layer (14) and wherein the outer layer (18) is arranged at least partly upon and in contact with the middle layer (16), wherein the base layer (14) comprises a metal, wherein the middle layer (16) comprises a metal oxide, and wherein the outer layer (18) is porous and comprises a material selected from the group comprising electrically conductive carbon compounds such as, more particularly, graphite or carbon nanotubes (CNTs), organic electrical conductors and base metals, and wherein electrical contacts can be formed with the base layer (Continued)

(14) and outer layer (18) for a conductivity measurement and/or a resistance measurement. Such a sensor (10) provides a high sensitivity with a high selectivity already at ambient temperature and is furthermore producible especially cost-saving. The present invention further refers to a method for producing a sensor (10). The present invention further refers to the use of a sensor (10) according to the invention as gas sensor and/or as liquid sensor.

13 Claims, 6 Drawing Sheets

(56) References Cited

U.S. PATENT DOCUMENTS

| | | | | |
|---|---|---|---|---|
| 4,482,882 | A | * | 11/1984 | Luder .................. G01N 27/121 338/308 |
| 4,541,904 | A | | 9/1985 | Lüder et al. |
| 4,916,075 | A | | 4/1990 | Malmros et al. |
| 5,001,453 | A | * | 3/1991 | Ikejiri .................. G01N 27/121 338/35 |
| 2002/0118027 | A1 | | 8/2002 | Routkevitch et al. |
| 2004/0033679 | A1 | * | 2/2004 | Jacobson ............... B82Y 10/00 438/510 |
| 2005/0224360 | A1 | * | 10/2005 | Varghese ............... B82Y 30/00 205/171 |
| 2009/0324810 | A1 | * | 12/2009 | Serikawa ............ C02F 1/46109 427/78 |
| 2010/0139365 | A1 | | 6/2010 | Fix et al. |

FOREIGN PATENT DOCUMENTS

| | | |
|---|---|---|
| DE | 102006020253 B3 | 11/2007 |
| DE | 102007040726 A1 | 3/2009 |
| DE | 102008046319 B3 | 12/2009 |
| JP | A SHO57-078104 | 5/1982 |
| JP | A SHO59-15316 | 9/1984 |
| JP | H01145560 | 6/1989 |
| JP | A 2006-526279 | 11/2006 |
| JP | A 2007-322342 | 12/2007 |
| JP | A 2010-096694 | 4/2010 |
| WO | WO 2004/109807 A2 | 12/2004 |

OTHER PUBLICATIONS

International Preliminary Report on Patentability Chapter I issued in corresponding International Application No. PCT/EP2012/070066 dated Apr. 15, 2014.

International Search Report issued in corresponding International Application No. PCT/EP2012/070066 dated Jul. 1, 2013.

Ding et al: "Hyrdogen sensors based on aligned carbon nanotubes in an anodic aluminum oxide template with palladium as a top electrode". Sensors and Actuators B: Chemical: International Journal Devoted to Research and Development of Physical and Chemical Transducers, Elsevier S.A. Switzerland, Bd. 124, Nr. 1, May 16, 2007 (May 16, 2007), Seiten 12-17, XP022080497, ISSN: 0925-4005, DOI: 10.1016/J.SNB. 2006.11.034.

Manabu Takeuchi (et al), Electrical Properties of Anodized Aluminum Gas Sensors, Analytical Chemistry Symposia Series, Sep. 19, vol. 17, pp. 422-427.

* cited by examiner

SENSOR AND METHOD FOR MANUFACTURING A SENSOR

This application is a national phase application under 35 U.S.C. § 371 of International Application No. PCT/EP2012/070066, filed Oct. 10, 2012, which claims priority to German Patent Application No. 10 2011 054 501.8, filed on Oct. 14, 2011; the disclosures of which are all hereby incorporated by reference herein.

FIELD OF THE INVENTION

The present invention relates to a sensor, especially a gas sensor and/or a liquid sensor. The present invention further relates to a process for producing a sensor.

BACKGROUND OF THE INVENTION

Sensors, for example gas sensors, are widely used and are known for many fields of use. For example, there are known gas sensors based on the principle of liquid electrochemistry or on the principle of thermal conduction. There are also known gas sensors which exploit MOS capacitors and capacity measurements, Schottky diodes and current/voltage measurements, field-effect transistors, heated semiconductive metal oxides and electrical resistance or conductivity measurements, or else ion-conducting membranes and potential measurements, as the detection principle.

The aforementioned gas sensors entail usually complex and hence costly production processes and therefore have a high cost, which means that they are only of limited usability for a multitude of applications and of restricted economic viability. Moreover, many of the aforementioned gas sensors have a not insignificant cross-sensitivity for constituents present in a gas other than those to be detected, for instance further gases, such that the measurement results obtained can have only limited accuracy. Furthermore, many gas sensors known from the prior art have an elevated working temperature, in some cases considerably elevated, compared to room temperature, which necessitates heating of the sensor for a measurement. As a result, sensors of this kind may under some circumstances be usable only to a limited degree, if at all, for portable applications. Moreover, as a result of high working temperatures, especially in the measurement of hydrogen, there is a risk of explosion, which should understandably be avoided. Furthermore, the need to heat a sensor always also leads to an elevated power consumption, which means that the sensor can only be of limited economic viability and, in addition, only of limited utility for portable applications. Moreover, the heating requires an additional heating layer or heating coil and electrical leads or electrical connections on the sensor.

DE 10 2006 020 253 B3 describes a titanium dioxide sensor for measurement of concentrations of reducing gases such as hydrogen, methane or ammonia. The sensor according to this publication consists of at least two layers of polycrystalline titanium dioxide on any desired substrate, which should withstand the final temperatures of approximately 500° C. for crystallization of the layers. The at least two layers of titanium dioxide are arranged one on top of the other, with the outer lamina, which forms the surface of the sensor toward the gas space, provided with catalyst particles present in the region of the particle interfaces, and the layer immediately beneath enriched with an alkali metal. A sensor of this kind should contain principally anatase titanium dioxide. The corresponding layers are produced by spin-coating or another sol-gel coating step.

A disadvantage of such a sensor is that, for a reliable and highly accurate measurement, it requires working temperatures within a range above room temperature, which is disadvantageous especially for a measurement of hydrogen and can also make the measurement inconvenient and costly. Furthermore, the production process for such a sensor is inconvenient and hence costly, which also makes such a sensor costly.

SUMMARY OF THE INVENTION

It is therefore an object of the present invention to provide a sensor producible in a simple and/or inexpensive manner, and/or which is usable in a simpler, more robust and/or less expensive manner, and/or has a good sensitivity and selectivity within a wide temperature range encompassing the ambient temperature.

This object is achieved by a sensor according to claim 1. This object is also achieved by a process for producing a sensor according to claim 9. Preferred embodiments of the invention are specified in the dependent claims.

The present invention provides a sensor having a layer arrangement, wherein the layer arrangement comprises at least a base layer, a middle layer and an outer layer, wherein the middle layer is arranged at least partly upon and in contact with the base layer and wherein the outer layer is arranged at least partly upon and in contact with the middle layer, wherein the base layer comprises a metal, wherein the middle layer comprises a metal oxide, and wherein the outer layer is porous and comprises a material selected from the group comprising electrically conductive carbon compounds such as, more particularly, graphite or carbon nanotubes (CNTs), organic electrical conductors and base metals, and wherein electrical contacts can be formed with the base layer and outer layer for a conductivity measurement and/or a resistance measurement.

A "layer arrangement" may be understood in the context of the present invention to mean, more particularly, an arrangement composed of a plurality of successive layers. The individual layers may each take the form of a single layer or be formed from a multitude of component layers. In addition, the individual layers may be arranged directly on top of another and hence, more particularly, may be in electrical contact with one another, or else may be arranged one on top of another and bonded to one another, or more particularly may be in electrical contact, through a suitable intermediate lamina or intermediate layer. A layer as such may also be understood in the context of the present invention to mean, more particularly, any lamina, which may have any suitable shape, thickness and configuration.

A "base layer" in the context of the present invention may especially be understood to be a carrier layer on which further layers are arranged. The base layer may be self-supporting, i.e. may, for instance, itself have adequate stability to impart adequate stability, for instance, to itself or else to the layer arrangement. In addition, the base layer may be configured as the lowermost layer of the sensor, or else have been applied to a further substrate. In this case, the substrate is especially electrically nonconductive and may be formed, for instance, from plastic, glass or a ceramic. The base layer here may especially comprise a metal or be constructed from the metal. For example, the base layer may consist of a metal. Especially when the metal of the base layer has a sufficient thickness, it is possible to omit a substrate on which the base layer is arranged. The base layer in the inventive sensor may serve especially as a lower electrode or reverse electrode, with which electrical contacts can be formed in a manner known per se.

A "middle layer" in the context of the present invention may especially be understood to mean a layer arranged between the base layer and the outer layer.

The middle layer is preferably arranged directly upon the base layer and is thus in contact therewith. In this case, the middle layer may cover the base layer preferably completely or else only partly, and is thus, more particularly, at least partly arranged upon the base layer. The middle layer here comprises a metal oxide or is, for instance exclusively, formed therefrom. More preferably, the middle layer comprises the oxide of the metal which can be used in the base layer. The middle layer may especially be porous and especially have open porosity. This gives rise to an increased contact area between the middle layer and the base layer, and between the middle layer and the outer layer. It is especially possible here for the middle layer to be intimately intermeshed with the base layer, in order to ensure better electrical contact between middle layer and base layer. The structure of the middle layer and of the base layer especially achieves a long three-phase boundary at which the molecules of the gas phase, in the case of use as a gas sensor, can chemically react, for instance, with the atomic lattice units of the outer layer and the atomic lattice units of the middle layer. The middle layer may have, for example, a specific conductivity within a region of $\leq 0.00001$ ohm$^{-1}$ m$^{-1}$, and can thus be essentially electrically nonconductive. The conductivity of the middle layer may also be dependent on the electrical voltage or be adjustable via the electrical voltage.

An "outer layer" in the context of the present invention may especially be understood to mean a layer which, as the uppermost layer, at least partly covers the layer arrangement or especially the middle layer. Thus, the outer layer is preferably arranged directly upon and in contact with the middle layer. The outer layer here may preferably fully cover the middle layer, or else may cover only a portion of the middle layer.

The outer layer is thus especially the layer which comes into or is in contact with the substance to be analyzed, especially a fluid, for instance a gas or a liquid, and thus serves as the upper electrode or front electrode in the inventive sensor. As such, it can especially be provided with electrical contacts in a manner known per se. The outer layer is especially porous and especially has open porosity, in order to enable access of the substances to be detected to the middle layer or to the interface between the middle layer and outer layer. The outer layer also comprises or consists of a material selected from the group comprising electrically conductive carbon compounds such as, more particularly, graphite or carbon nanotubes, organic electrical conductors and base metals, where the latter may advantageously comprise a conversion layer which may especially be arranged upon the opposite side of the outer layer from the middle layer, or on side regions of the outer layer.

A conversion layer in the context of the invention may especially be a layer which is effected through a chemical or electrochemical, especially oxidative, reaction of the metal in a fluid such as, more particularly, a liquid or a gas. In the case of the outer layer in particular, the conversion layer may be a passivation layer. A passivation layer may refer in the context of the present invention especially to a protective layer which forms spontaneously on the base metal, which forms, for example, under air and which can also be altered deliberately in order to increase the protective effect. The passivation layer thus forms, for example, when the metal is exposed to an oxidative environment, for example the ambient air, thus resulting in oxidation of the metal. Consequently, the conversion layer or passivation layer is especially a metal oxide and can thus protect the metal layer from further oxidation or at least distinctly slow this further oxidation, which can increase the lifetime of the sensor. At the same time, the conversion layer should not be fluid-impervious, in order to enable free fluidic mobility into the pores of the outer layer, such that the porosity of the outer layer is unaffected.

Consequently, the outer layer is especially formed from an electrical conductor which serves as a porous matrix and is either not a metal or else is not a noble metal. The outer layer, in the case of use of a metal, may especially be a metal which forms a conversion layer or passivation layer.

The inventive sensor allows, through formation of electrical contacts with the base layer and the outer layer, and through the application of a voltage to the base layer and outer layer, a qualitative and quantitative determination of substances to be detected through a conductivity measurement and/or a resistance measurement. In detail, a signal can be generated, for example, from an electrical AC current measurement of the resistance or of the conductivity.

The layer arrangement of the sensor, or more particularly the middle layer and outer layer, may have an ohmic contact at the junction thereof, which forms a linear current-voltage characteristic with reference to a conductivity or resistance measurement. This can be achieved, more particularly, by virtue of the fact that the work function, i.e., more particularly, the energy difference between the vacuum level and the Fermi energy, of the outer layer is lower than that of the middle layer, or by virtue of the fact that the electrons can tunnel through a very thin tunnel barrier between the outer layer and the middle layer when the work function of the outer layer is greater than that of the middle layer. This is a significant advantage with respect to the Schottky diodes known from the prior art, which exhibit a nonlinear diode characteristic with distinct dependence of the current on the voltage, the effect of which is a possible variance such as, more particularly, scatter or variation in the zero signal and a greater measurement uncertainty. Consequently, a distinct improvement in measurement accuracy and also a distinct simplification in calibration is possible with the inventive sensor by virtue of a linear current-voltage characteristic.

In the inventive sensor, the conductivity is especially determined by the layer structure. Essential factors for the function and the measurement characteristics of the sensor may especially be interfacial reactions at or close to interfaces of a conductor and an oxide, i.e. the interface of the middle layer and the outer layer. For instance, adsorbates form in air upon the oxide of the middle layer, for example through chemisorption of oxygen. These react with the gases to be detected when particular voltages are applied to the sensor or to the base layer and the outer layer. It is also possible for electroactive adsorbates to form at the interface with the gases to be detected, these altering the electrical conductivity through absorption or release of electrons. This layer arrangement constitutes, more particularly, a resistor or a capacitor.

In the inventive sensor, a change in the frequency of the AC voltage applied can especially enable a qualitative measurement of a substance in a substance mixture, for instance of a gas in a gas mixture. Through a suitable selection of the appropriate frequency, it is possible here to discriminate various substances, which enables the detection of further gases. A qualitative measurement of this kind is also likewise possible in the case of selection of the voltage applied in a measurement. Thus, a qualitative measurement results, for example, from a change in the frequency and/or voltage, whereas especially the magnitude of the change in conductivity or change in resistance constitutes a measure for a quantitative measurement. This gives rise, in principle, to the novel possibility of controlling the sensitivity of the sensor, for instance, for different gases or other substances to be detected via the voltage or frequency applied, and of thus reducing the cross-sensitivity for other substances, for instance gases. It is thus likewise possible to enable a very good selectivity for the substances to be detected. For example, hydrogen and relative humidity or water, as non-limiting examples, can be detected, for instance, specifically by different voltages, or individually and independently in high selectivity and sensitivity, even alongside one another in a mixture.

An inventive sensor thus offers an excellent selectivity with simultaneously high sensitivity, even in the case of measurement of a wide variety of different substances, for instance a wide variety of different gases, for instance hydrogen, oxygen, carbon monoxide, carbon dioxide, or else liquids, for instance water or alcohol, for example in a gas mixture or liquid mixture in variable concentrations, the above enumeration being nonexclusive. The sensor allows, through a suitable selection of the operating conditions, for instance frequency and voltage, the measurement of substances desired without disruptive influences from other substances. Thus, both qualitative and quantitative measurements of high quality are possible in a simple manner.

In the inventive sensor, it is also possible, by virtue of the fact that costly noble metals can be omitted entirely, or else by virtue of the fact that the use thereof can at least be distinctly limited, to considerably lower the production costs for an inventive sensor and the costs of the sensor as such.

Furthermore, by omitting noble metals, it is possible to overcome the disadvantage that noble metal contacts such as, more particularly, platinum experience heating when contacted with hydrogen, for instance, as the substance to be analyzed in air. The particular reason for this heating lies in a catalytic reaction, namely the combustion of hydrogen to water. This leads to drift in the measurement signal. Consequently, by dispensing with noble metals as the outer layer or outer layer matrix in accordance with the invention, it is possible to prevent such drift, since no disruptive catalytic heat of reaction, for example, is released on contacting with hydrogen in air. Consequently, there is no change in the temperature of the sensor. As a result, it is possible in accordance with the invention to further increase the measurement accuracy even in the case of very long measurement cycles.

According to the invention, it is also possible to overcome a further disadvantage of Schottky diodes in particular, which arises through the use of noble metal contacts and the associated formation of water. This is because the water formed also affects the electrical conductivity of the diode. In the prior art, this results in the problem that water-blocking membranes can be used only to a limited degree, if at all, since the water of reaction formed as described above would no longer be able to diffuse away from the interior of the sensor. Consequently, according to the prior art, it is not possible to effectively exclude air humidity which acts on the sensor from the outside. By dispensing with noble metal contacts between outer layer and middle layer through a noble metal layer in accordance with the invention, through the lack of formation of water of reaction, to equip or envelop or coat the sensor with moisture-repellent membranes, which can constitute a significant advantage, for example for the measurement accuracy, for use, for example, as a hydrogen sensor.

In addition, the inventive sensor enables good measurement results even at room temperature or ambient temperature, such that it is possible to entirely dispense with heating. Thus, the inventive sensor can be operated particularly inexpensively and reliably, and also offers advantages in use for mobile applications. This is because it is possible to dispense with energy storage means, some of which are heavy and space-consuming, or greatly restrict the demand therefor. Furthermore, the inventive sensor, by virtue of its simple layer structure, is producible in a particularly simple and inexpensive manner, which also makes the sensor as such particularly inexpensive and hence become economically viable for extensive fields of use. The sandwich arrangement of the layers enables a particularly simple, robust and small construction of the sensor. More particularly, the sensor thickness may be between ≥100 µm and ≤500 µm, in which case the outer layer may have a thickness within a region of ≤4 µm and/or the middle layer may have a thickness within a region of ≤10 µm and/or the base layer may have a thickness within a region of ≤500 µm. This is a considerable advantage over the prior art, especially over the electrochemical sensors. As well as the marked simplicity of the layer structure, it is possible in this way to permit a particularly great variety of uses and freedom to design through the low thickness and the associated potential for miniaturization. The inventive sensor can thus be integrated directly into desired components as a component part in a simple manner.

In an embodiment, the base layer may comprise at least one metal selected from the group comprising or consisting of titanium, vanadium, chromium, zirconium, niobium, molybdenum, tantalum and tungsten, or an alloy of one or more of these metals with one or more of these or further metals, for example aluminum, palladium, manganese, iron, nickel, cobalt, copper or rare earth metals. Among the aforementioned metals, titanium in particular is advantageous. Substances of this kind can spontaneously form a conversion layer in an oxidizing atmosphere or, more particularly, be induced to form a conversion layer by an electrochemical reaction, by virtue of which they are protected from oxidation. Therefore, the base layer in this embodiment has a particularly long lifetime. In addition, it is possible with such materials to form very stable layers even in low thicknesses, such that it is possible to omit a further carrier substrate upon which the base layer is arranged.

In a further embodiment, the middle layer may be a conversion layer of the base layer. In this embodiment, the inventive sensor can be produced in a particularly simple and inexpensive manner. For example, the conversion layer can be produced via an electrochemical anodization of the base layer, i.e. can in principle be produced by a deliberate and especially specific and defined chemical or electrochemical treatment. This is a process which has good controllability, is known, is inexpensive, and can be used without any problem even on the industrial scale. In this case, the middle layer is thus formed from the metal oxide of the base layer. Furthermore, in this configuration in particular, the middle layer is particularly porous, in that the pore sizes can be set within a range from ≥10 nm to ≤5000 nm and a particularly good and large-area contact is present between the base layer and the middle layer, which can further improve the measurement results. The pore sizes can be set, for example, through the selection of suitable parameters in the application or production of the middle layer. A conversion layer here, in the context of the invention, may especially be a layer which can be produced via an electrochemical or chemical, especially oxidative, reaction of the base layer in a fluid such as, more particularly, a gas or a liquid.

In a further embodiment, the outer layer may have been produced at least partly from colloidal graphite. An outer layer of this kind in particular offers a good conductivity, which can allow a high sensitivity and selectivity of the sensor. Furthermore, an outer layer of this kind offers the advantage of easy and inexpensive applicability and a high stability against external influences. Furthermore, the use of an outer layer produced from colloidal graphite can provide a preferred matrix having a porosity, especially an open porosity, suitable for a multitude of applications, such that good measurement results are firstly possible through marked diffusibility of the substances to be analyzed at the interface between the middle layer and outer layer, and the sensor can also be adapted particularly efficiently to a wide variety of different substances to be analyzed, as will be explained later.

In a further embodiment, the pore width of the outer layer and/or of the middle layer may be within a range from $\geq 10$ nm to $\leq 5000$ nm. This can achieve enablement of particularly good accessibility of substances to be analyzed through the outer layer to the phase boundary of outer layer and middle layer. In addition, a particularly high sensitivity and selectivity can be achieved. Furthermore, such a pore width offers great stability, such that the lifetime of the outer layer or middle layer and hence of the sensor can be improved. The porosity can in turn be set through a suitable selection of the deposition conditions or of the conditions for production of the outer layer and/or of the middle layer.

In a further embodiment, the sensor may also comprise at least one additive arranged at least partly in the pores of the outer layer. Through the arrangement of such an additive, it is possible to adapt the inventive sensor to substances to be analyzed in a particularly simple and effective manner, in that, for instance, the properties of the outer layer can be altered or adjusted in a controlled manner. For example, the additive used may be a catalytically active substance which catalyzes a reaction of the substance to be detected which influences the conductivity of the layer arrangement, especially at the interface between the middle layer and outer layer, such that the sensor becomes selective for this substance in particular.

In a further embodiment, the at least one additive may comprise or consist of a noble metal such as, more particularly, gold, platinum, palladium, rhodium, iridium, ruthenium or an alloy of one or more of the aforementioned metals. Metals of this kind in particular can serve selectively as catalysts for defined substances to be detected. For example, it is possible with gold particles of a size which may be within a range from about $\geq 2$ nm to $\leq 4$ nm, for example 3 nm, to selectively detect carbon monoxide in air with great accuracy.

In a further embodiment, the at least one additive may have been arranged on a carrier material, for example on activated carbon, on gamma-alumina or on titanium dioxide. In this way, the at least one additive is present in defined form, which likewise allows defined measurement results and an improved measurement accuracy. Furthermore, in this embodiment, it is possible to immobilize the additive(s) in a particularly simple and reliable manner in the pores of the outer layer, such that these are arranged in the pores of the outer layer even after a prolonged duration of use. Thus, in this embodiment too, the lifetime of the sensor can be improved further. A further advantage of the use of a carrier material is that the additive can be used in stabilized form, in which a defined and desired catalytic activity is established. In this context, the carrier material may have, for example, a Vickers hardness within a range from $\geq 80$ HV10 to $\leq 150$ HV10, where the hardness may be dependent on the material used. In detail, without limitation, the following may be suitable here: titanium with 150 HV 5/30, tungsten with >500 HV 30, molybdenum with 200-220 HV30, chromium with 1100-1300 HV 30 or vanadium with 80-150 HV10. In this way, the production process, especially in the case of simultaneous production of a multitude of sensors, can be made easier, since the carrier material has, for instance, a cuttable strength and need not be sawn.

The present invention further provides a process for producing an inventive sensor, comprising the process steps of:

a) providing a base layer, the base layer comprising a metal, b) applying a middle layer to at least a portion of the base layer, in such a way that the middle layer is arranged at least partly upon and in contact with the base layer, the middle layer comprising a metal oxide, and c) applying an outer layer to at least a portion of the middle layer, in such a way that the outer layer is arranged at least partly upon and in contact with the middle layer, the outer layer being porous and comprising a material selected from the group comprising electrically conductive carbon compounds such as, more particularly, graphite or carbon nanotubes, organic electrical conductors and base metals.

The process according to the invention thus comprises essentially just three process steps, namely the provision of a base layer, the application of a middle layer and the application of an outer layer. Thus, the process according to the present invention is implementable in a particularly simple, rapid and inexpensive manner.

At the same time, the process according to the invention has good controllability and is also of good suitability for mass production.

After completion of process step c), the layer arrangement of the sensor is essentially complete. In order that the sensor works as desired, for instance by resistance measurements or by conductivity measurements, it is possible to form electrical contacts by means of electrical connections with the outer layer and the base layer in particular. For example, one contact each may be provided at the outer layer and at the base layer, and this can be connected or is connected via an electrical conductor, for instance a thin metal wire, to a voltage source for application of a voltage. Furthermore, it is possible in each case to secure an electrical conductor which can be connected or is connected to a voltage source directly to the base layer or the outer layer, for instance by soldering, bonding, welding or adhesive bonding. In addition, a current measuring device or a resistance measuring device may appropriately be provided.

With regard to further advantages of the process according to the invention or of the sensor producible by the process according to the invention, reference is hereby made to the details for the inventive sensor.

In the context of a preferred embodiment, the process may especially comprise, with regard to process steps a) and b), the process steps of:

d) providing an electrolyte;

e) contacting a base layer with the electrolyte;

f) contacting an electrode with the electrolyte, wherein g) the base layer is connected as the anode and the electrode as the cathode, h) applying a voltage between the electrode and the base layer for a predetermined period to form an oxide layer as the middle layer;

i) removing the base layer together with the middle layer formed in step h) from the electrolyte;

j) applying an outer layer to at least part of the middle layer.

Through the process according to the invention, it is possible to produce the inventive sensor in this embodiment in a particularly simple and inexpensive manner. In detail, the middle layer is produced by electrochemical anodization of the base layer. In this case, the metal of the base layer is oxidized during the anodization, and the oxide of the corresponding metal of the base layer is therefore produced as the middle layer.

An electrochemical anodization is a process of good controllability and good definability, which does not require any complex constructions. In this way, it is possible to apply, in an exactly defined manner, a defined conversion layer or middle layer upon the base layer. At the same time, the process according to the invention, by virtue of its simplicity and inexpensiveness, is also suitable for mass production and, in addition, the sensors produced are usable and economically viable for a particularly great multitude of applications.

In detail, in step d), an electrolyte is provided. This may, for example, be an alkali or acid. More preferably, the electrolyte may comprise an acid, for example sulfuric acid. In principle, it may be preferable to provide a liquid electrolyte. In this case, the electrolyte, for example sulfuric acid, can be used especially in a concentration range from $\geq 0.1$ mol/liter to $\leq 16$ mol/liter, for example 14 mol/liter. The electrolyte can be provided here, for example, as an electrolyte bath in a vessel, for instance a trough.

In step e), a base layer is contacted with the electrolyte. This means that the material which forms the base layer in the finished sensor or in the layer arrangement of the sensor is contacted with the electrolyte, i.e., for example, is arranged within the electrolyte, for example by dipping. For example, a metal foil may be used as the base layer; thus, for instance in the case of use of titanium for the base layer, a titanium foil or a titanium sheet may be contacted with the electrolyte, i.e. may be dipped, for example, into the electrolyte.

In step f), in this embodiment of the process according to the invention, an electrode is contacted with the electrolyte, i.e., for example, likewise dipped into the electrolyte. In the context of the invention, this is intended to mean, more particularly, that, as well as the base layer, a further electrically conductive material, for example a graphite electrode, is contacted with the electrolyte by being dipped into it.

In the course of this, or in a further step, according to step g), the base layer is connected as the anode and the electrode as the cathode. This can be achieved, for example, by, in a step h), applying a voltage between the electrode and the base layer to form an oxide layer as the middle layer. This allows formation of an oxide layer as conversion layer of the base layer by electrochemical anodization, and this forms the middle layer. For example, it is possible to apply a voltage within a range from 50 V to 200 V, especially 170 V.

In addition, an applied voltage according to process step h) is maintained for a predetermined period. In the context of the present invention, this is intended to mean, more particularly, that a voltage of any size is maintained over a defined period, for instance one hour, and the size of the voltage, for example, may change during process step h) or else may be kept constant. By virtue of the maintenance of an applied voltage, a growing conversion layer or middle layer is thus applied. The thickness of the conversion layer or middle layer applied corresponds, for example, to the duration of the voltage applied and hence to the duration of the flowing current and to the size of the flowing current.

It is clear that, in this embodiment of the above-described process, the entire surface of the base layer is converted or can be covered with a middle layer. If, for instance, defined structures of a middle layer are to be provided, the base layer, for instance through the provision of corresponding masks, can be protected from a complete conversion, in order thus, for instance, to produce the desired structure.

In principle, the above-described process is what is called a PEO process (plasma electrolytic oxidation). In this process, electrical discharges occur, which can lead to occurrence of gaseous oxygen, which promotes or enables the anodization. Thus, in accordance with the invention, more particularly, production of the middle layer may take place by plasma electrolysis, which can be implemented especially at applied voltages of $\leq 50$ V, preferably of $\leq 100$ V. In this way, a process for production of the layer arrangement for the inventive sensor in which very high temperatures and partial pressures, for instance of oxygen, occur locally at the base layer is used, which allows a particularly effective process. In this configuration, electrical discharges are thus used in a controlled manner with spark formation.

Another advantage of the anodization process employed in this configuration is that very intimate contact arises between the middle layer and the base layer, which has a positive influence on the measurement characteristics of the sensor.

Especially during process step h), the current density of the flowing current, in an advantageous embodiment, may have been or may be limited to a region of 200 mAcm$^{-2}$. For example, for an electrolyte vessel of 50 ml and a base layer of size 5 mm×5 mm, a maximum current of 200 mA may be advantageous. At the same time, the current may be limited, especially at the start of the anodization. The voltage can be increased over the course of the anodization when the flowing current falls, such that the anodization current remains constant. Such a limitation of the current can serve, more particularly, to limit the heating of the electrolyte, which can arise, for example, through the electrical discharge. This can improve the accuracy of control of the anodization process through essentially constant temperatures.

In this regard, it may be advantageous in a further configuration that the electrolyte is cooled, especially during step h). For example, the electrolyte can be stirred, for instance using a stirrer such as a magnetic stirrer, or it is possible to use cooling devices, for example an external circulation cooler. In this way, it is likewise possible to achieve the abovementioned advantages mentioned in relation to a constant anodization temperature.

This may also be possible through provision of electrolyte baths of appropriate size, in which the anodization is conducted. For example, the volume of the electrolyte bath may be greater than 200 ml/cm$^2$ of base layer area.

After the end of the conversion or the application of the middle layer, it is possible in process step i) to remove the base layer together with the middle layer formed in step h) from the electrolyte. For example, the arrangement of base layer and middle layer can be removed from an electrolyte liquid. Appropriately, the layer arrangement removed from the electrolyte can be cleaned to remove the electrolyte, for example by means of distilled water. Subsequently, the layer arrangement can be dried, for example by a thermal treatment at about 400° C., for example for a period of 20 s.

In a next step, in this embodiment, according to process step j), the outer layer is applied to at least a portion of the middle layer. This can be done in a wide variety of different ways. In the case of application of a colloidal graphite layer, for example, this can be applied, for instance, by a spray application or by a printing operation. In principle, however, all processes by which the corresponding outer layer is applied or can be applied to at least a portion of the middle layer are possible. The outer layer applied can then be after treated in a suitable manner, if necessary, for instance by drying, sintering or the like.

After completion of process step j), the layer arrangement of the sensor is essentially complete. In order that the sensor works as desired, for instance by resistance measurements or by conductivity measurements, it is again possible to form electrical contacts by means of electrical connections with the outer layer and the base layer in particular. For example, one contact each may be provided at the outer layer and at the base layer, and this can be connected or is connected via an electrical conductor, for instance a thin metal wire, to a voltage source for application of a voltage. Furthermore, it is possible in each case to secure an electrical conductor which can be connected or is connected to a voltage source directly to the base layer or the outer layer, for instance by soldering, bonding, welding or adhesive bonding. In addition, a current measuring device or a resistance measuring device may appropriately be provided, in order to be able to conduct detection of substances to be analyzed.

In this context, it will be apparent to the person skilled in the art that the aforementioned process steps can be conducted successively or simultaneously.

In a further embodiment, in step a), a multitude of base layer units secured to one another is provided, and, in steps b) and c), a multitude of sensor units is formed, and the individual sensor units are individualized after process step c), especially by means of a cutting tool. This is a particularly time-efficient and inexpensive process in order to be able to produce a multitude of sensor units or sensors.

A base layer unit in the context of the present invention may especially be a region of a base layer which serves as the sole base layer of a sensor unit to be produced or of a sensor. For this purpose, a base layer unit may be essentially divided from other base layer units, and may be connected merely by a land or a similar connecting means. The base layer units may also be fully secured to one another. In this case, the individual base layer units may be indicated or bounded by a groove or may merge into one another without marking.

The process according to the invention may, in this configuration, be conducted with all the base layer units together, such that process steps b) and c) are run through together. This forms a multitude of sensor units, the size and geometry of which may be defined essentially by the base layer units. The individual sensor units can then be individualized after process step c). For this purpose, a cutting tool which, for instance, severs the lands or grooves may be easpecially advantageous. In addition, however, it is also possible in principle to use other individualization devices, for instance sawing devices.

The present invention further provides for the use of an inventive sensor as a gas sensor and/or as a liquid sensor. The inventive sensor can be used, for example, for detection of substances, for instance gaseous substances or liquids, in a gas or gas mixture. In addition, the inventive sensor can be used, for instance, for detection of substances, for instance liquids or gases, in liquids or liquid mixtures. A nonlimiting example mentioned here is that of use in an organic solvent, for instance for monitoring of the residual moisture content or of dissolved gases. Through a suitable selection of the components of the layer arrangement of the inventive sensor, this is also suitable without any problem for long-term use in a wide variety of different gases and also liquids.

In principle, the specific field of use of the sensor may be dependent on the configuration of the sensor or on the reactivity of the outer layer.

With regard to further advantages of the sensor as a gas sensor and/or liquid sensor too, reference is made to the above remarks relating to the inventive sensor.

The invention is illustrated by way of example hereinafter with reference to the appended drawings by preferred embodiments, the features described hereinafter can constitute an aspect of the invention either individually or in combination, and the invention is not restricted to the drawings which follow and the description which follows.

BRIEF DESCRIPTION OF THE DRAWINGS

The figures show:

FIG. 2b an enlarged view of a section from FIG. 2a;

DETAILED DESCRIPTION OF THE INVENTION

Figure 1:
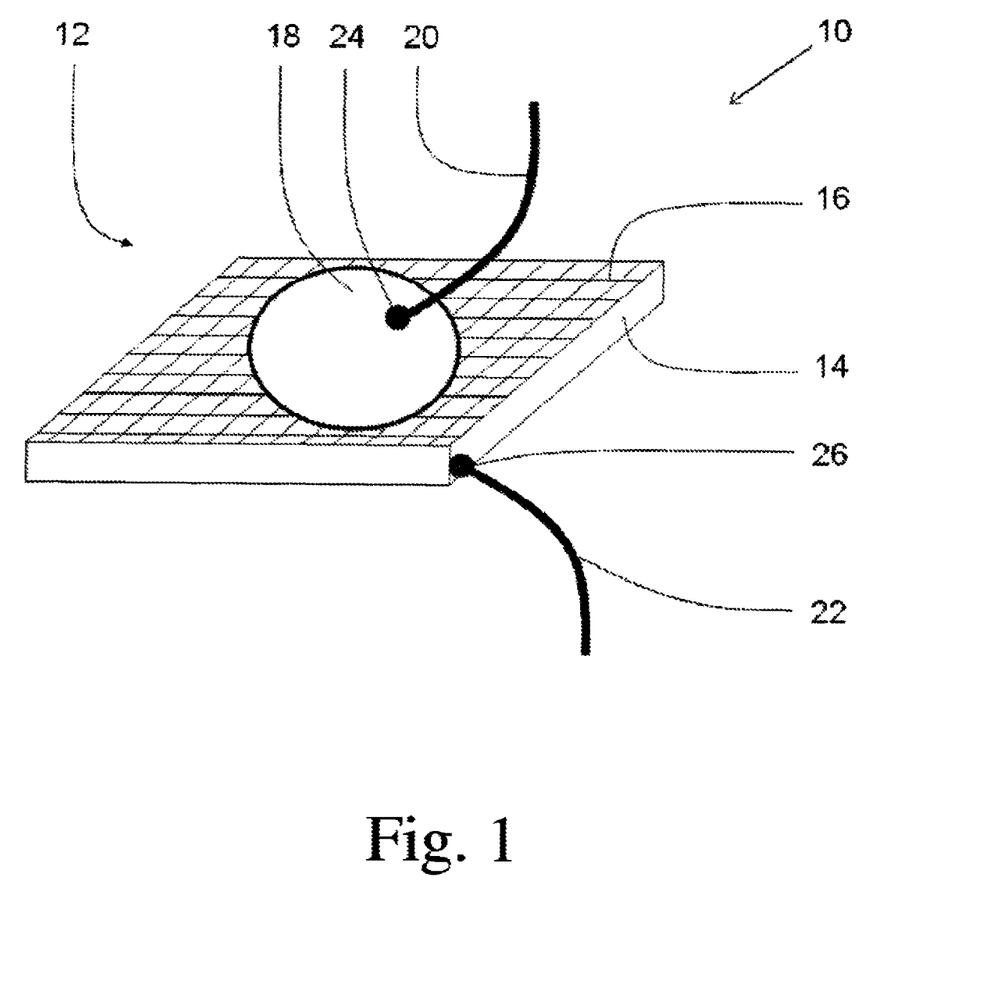
FIG. 1 a schematic view of an embodiment of an inventive sensor.

FIG. 1 shows a schematic embodiment of an inventive sensor 10. A sensor 10 of this kind can be used in all applications in which a substance to be detected, such as, more particularly, a gas to be measured or a liquid to be measured, is to be determined. One illustrative example given here is the use for air monitoring, for instance with regard to carbon monoxide or heating gas or cooking gas, for instance for private residences or industrial plants. In addition, environmental pollutants can be measured in the air. For the purely illustrative and nonlimiting case of a hydrogen sensor, this can be used, for example, in a hydrogen-operated vehicle, in the region of the hydrogen tank, in the environment of hydrogen lines or, for instance, in connection with the operation of fuel cells. In addition, the sensor 10 can generally be suitable, for instance, for reaction monitoring or for monitoring of laboratories or industrial processes. More particularly, the inventive sensor can be used as a gas sensor and/or as a liquid sensor. In this case, purely by way of example, the measuring of gases such as hydrogen or ozone or else of moisture may be advantageous. Applications for detection of alcohols, for instance as an lactometer, are also conceivable. The exact application may especially be dependent on the configuration of the sensor 10.

The sensor 10 according to FIG. 1 comprises a layer arrangement 12. This layer arrangement 12 has at least one base layer 14, a middle layer 16 and an outer layer 18. In FIG. 1, it is apparent that the middle layer 16 is arranged at least partly upon and in contact with the base layer 14 and the outer layer 18 is arranged at least partly upon and in contact with the middle layer 16. In this context, the middle layer 16 may entirely or partly cover the base layer 14. In addition, the outer layer 18 may entirely or partly cover the middle layer 16. The outer layer 18 is preferably somewhat smaller than the middle layer 16. For example, in the case of an area of the middle layer 16 of 5 mm×5 mm, a margin of 500 μm may be provided in each case. In this way, for example, the production process, for instance in the case of cutting over a large area for production of smaller sensor units or sensors 10, can be improved, or the ability of the sensor 10 to function after cutting can be ensured.

The base layer 14 especially comprises a metal which may be selected from the group comprising titanium, vanadium, chromium, zirconium, niobium, molybdenum, tantalum and tungsten, or an alloy of one or more of these metals with one or more of these or further metals, for example aluminum, palladium, manganese, iron, nickel, cobalt, copper or rare earth metals. The middle layer 16 comprises a metal oxide, especially a porous metal oxide, which may preferably be a conversion layer of the base layer 14 and/or have a pore size within a range from 10 nm to 5000 nm. The outer layer 18 is porous and may have pore widths within a range from 10 nm to 5000 nm. The outer layer 18 also comprises a material selected from the group comprising electrically conductive carbon compounds such as, more particularly, graphite or carbon nanotubes, organic electrical conductors and base metals, especially comprising a conversion layer or passivation layer. More particularly, the outer layer 18 has been produced at least partly from colloidal graphite.

The inventive sensor 10 may comprise, for example, at least one additive arranged at least partly within the pores of the outer layer 18. This at least one additive may comprise a noble metal such as, more particularly, gold, platinum, palladium, rhodium, iridium, ruthenium or an alloy of one or more of the aforementioned metals. With regard to the at least one additive, this may preferably be arranged on a carrier material, for example on activated carbon, on gamma-alumina or on titanium dioxide.

In order to be able to provide the sensor 10 with its function, electrical contacts can be formed with the base layer 14 and outer layer 18 for a conductivity measurement and/or a resistance measurement. For this purpose, for example, one electrical conductor 20, 22 each can be secured to the base layer 14 and to the outer layer 18, for instance via a solder point 24, 26. In addition, the sensor 10 can be connected, for example, to a resistance meter and/or a conductivity meter and an electronic evaluation unit, which evaluates the gas or liquid concentration to be measured on the basis of the data found.

The measurement range of an embodiment of an inventive sensor 10 wherein the front electrode or outer layer 18 consists of a layer of colloidal graphite of the Aquadag 18% name from HENKEL NEDERLAND BV, for hydrogen, may be 0.5% to at least the lower explosion limit in air when it is operated with a voltage of 3.5 V. The measurement range of the sensor 10 wherein the front electrode or outer layer 18 consists of a layer of colloidal graphite of the Aquadag 18% name from HENKEL NEDERLAND BV has, in relation to changes in the relative humidity in air, a measurement range from 0% to 100% at room temperature when it is operated at a voltage of 100 mV. The response times t90 may be less than 45 s for hydrogen and less than 6 s for moisture; the decay times may be less than 3 s for hydrogen and less than 20 s for moisture. It is thus apparent that the inventive sensor 10 can give very exact measurement results even at room temperature or ambient temperature.

Figure 2A:
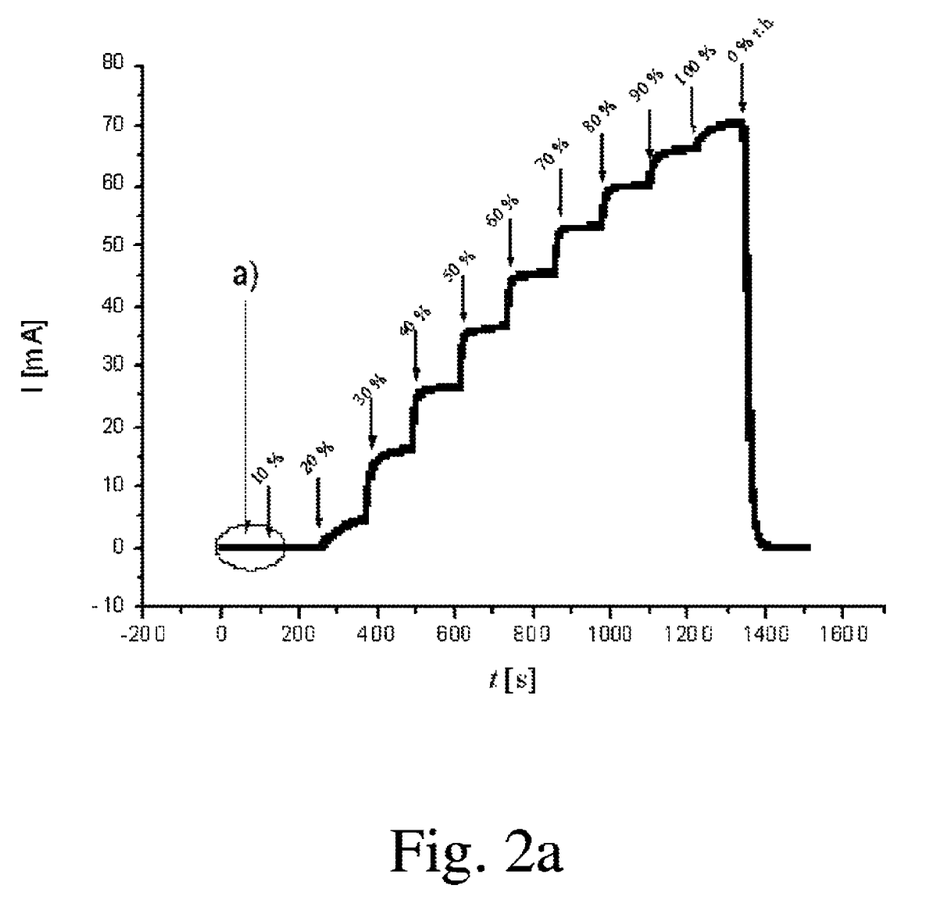
FIG. 2a a diagram showing, by way of example, the current flowing through one embodiment of the sensor as a function of time with variation of the relative air humidity measured.
Figure 2B:
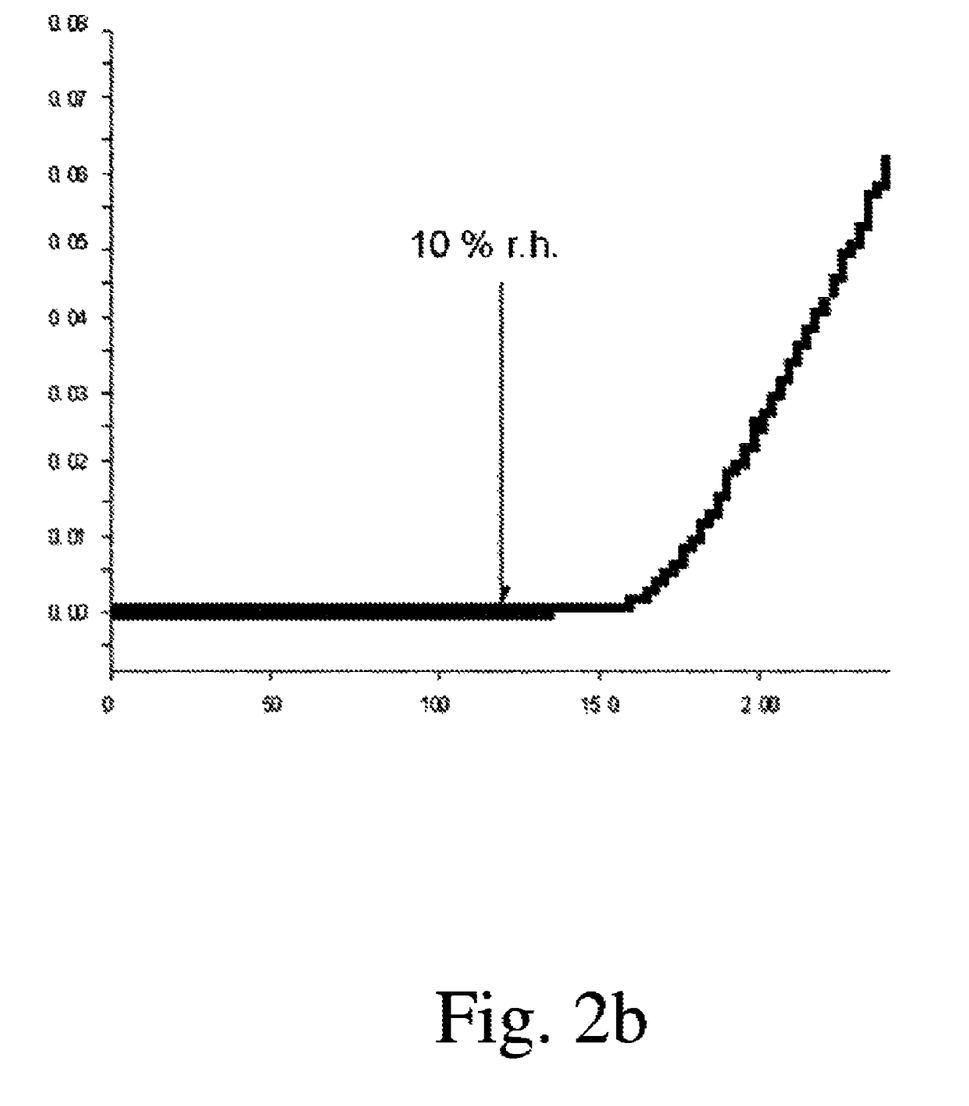

FIG. 2 shows a diagram which shows the current I through one embodiment of the sensor 10 as a function of time t on variation of the relative air humidity (r.h., relative humidity), and the sensor 10 is thus especially selective for air humidity. The section of FIG. 2a shown in enlarged form in FIG. 2b, which is indicated in FIG. 2a by a), shows an enlargement within a range from 0 to 200 seconds. It is apparent that the sensor 10 detects the moisture present even after a short response time and has a measurement range of essentially 0% to 100% moisture. The moisture is detectable here by a measurement of current.

Figure 3:
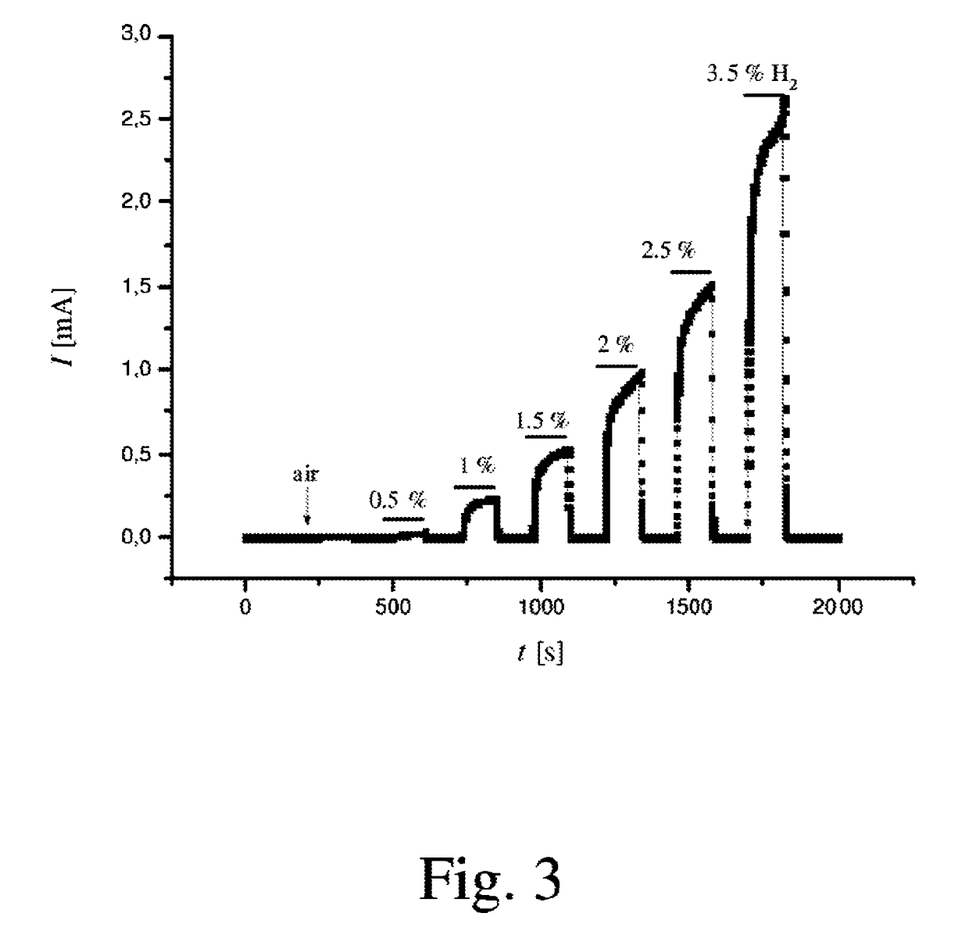
FIG. 3 a diagram showing, by way of example, the current flowing through one embodiment of the sensor as a function of time with variation of the hydrogen concentration measured in air.

FIG. 3 shows a diagram showing the current I through an embodiment of the sensor 10 as a function of time t on variation of the hydrogen concentration (x % $H_2$) in air. In this figure too, it is apparent that, even after short response times, even small hydrogen concentrations, which are sufficient for a multitude of applications, are detectable by a measurement of current.

Figure 4:
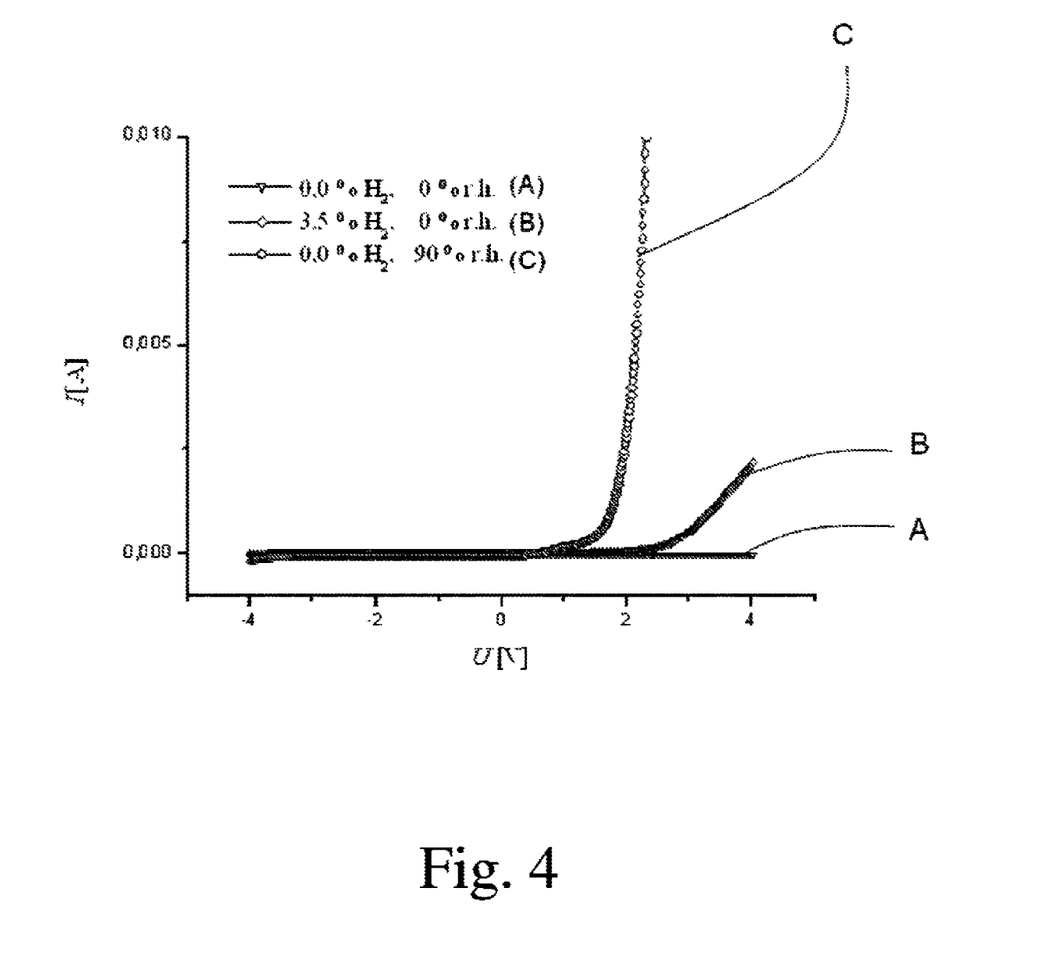
FIG. 4 a diagram showing, by way of example, a characteristic of one embodiment of the inventive sensor, and FIG. 5 a schematic view of a multitude of base layer units for production of a multitude of inventive sensors.

FIG. 4 shows a characteristic of one embodiment of a sensor 10 having an outer layer 18 of graphite. In detail, the current I is plotted against the voltage U in FIG. 4. Curve A shows a measurement in the absence of $H_2$ and moisture in air, curve B shows the characteristic at 3.5% $H_2$ and 0% relative humidity, and curve C shows the characteristic at 0.0% $H_2$ and 90% relative humidity. It is apparent from the diagram in FIG. 4 that, through a variation in the voltage, it is possible to selectively detect hydrogen and moisture independently of one another and alongside one another by a measurement of current.

A production process may especially comprise the following process steps:

a) providing a base layer 14, the base layer 14 comprising a metal, b) applying a middle layer 16 to at least a portion of the base layer 14, in such a way that the middle layer 16 is arranged at least partly upon and in contact with the base layer 14, the middle layer 14 comprising a metal oxide, and c) applying an outer layer 18 to at least a portion of the middle layer 16, in such a way that the outer layer 18 is arranged at least partly upon and in contact with the middle layer 16, the outer layer 18 being porous and comprising a material selected from the group comprising electrically conductive carbon compounds such as, more particularly, graphite or carbon nanotubes, organic electrical conductors and base metals.

More preferably, a process for producing an inventive sensor 10 may comprise the following steps:

d) providing an electrolyte;

e) contacting a base layer 14 with the electrolyte;

f) contacting an electrode with the electrolyte, wherein g) the base layer 14 is connected as the anode and the electrode as the cathode, h) applying a voltage between the electrode and the base layer 14 for a predetermined period to form an oxide layer as the middle layer 16;

i) removing the base layer 14 together with the middle layer formed in step h) from the electrolyte;

j) applying an outer layer 18 to at least part of the middle layer 16.

The electrolyte used here may be an alkali or acid, especially an acid, within a concentration range from ≥0.1 mol/liter to ≤16 mol/liter, and/or a voltage within a range from ≥50 V to ≤200 V, especially 170 V, may be applied. In order to achieve cooling of the electrolyte, the current density of the flowing current can be limited to a region of ≤200 mAcm$^{-2}$ and/or the electrolyte may be cooled during step h).

Preferably, in step a), a multitude of base layer units secured to one another can be provided, and, in steps b) and c), a multitude of sensor units or sensors is formed, and the individual sensor units are individualized after process step c), especially by means of a cutting tool. This is shown in FIG. 5.

Figure 5:
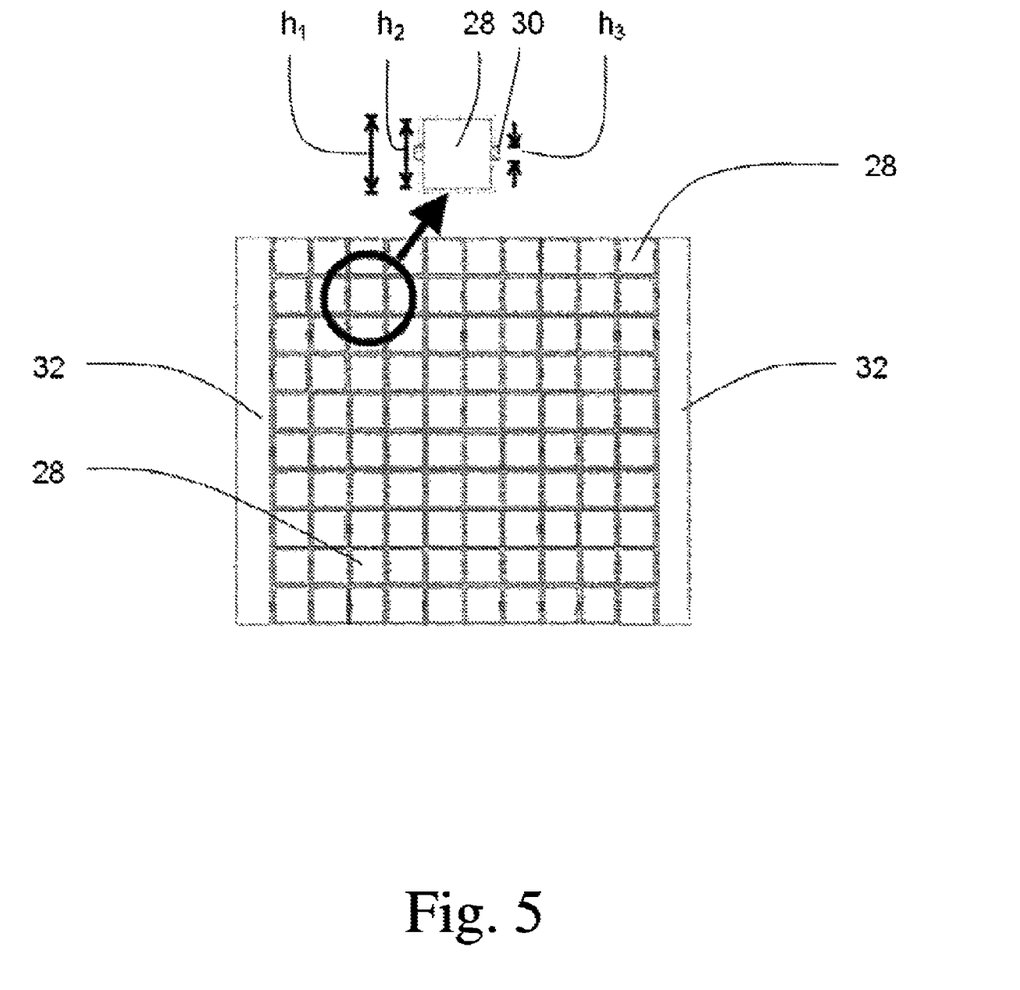

FIG. 5 shows a multitude of base layer units 28, for instance in a number of one hundred, which take the form, for example, of a foil and can serve as a precursor for sensor units or sensors 10. The individual base layer units 28 are, according to FIG. 5, connected to one another via lateral lands 30 and by fixing strips 32. The fixing strips 32 serve, more particularly, to hold or manipulate the arrangement of base layer units 28 in a processing plant and for supply of current in a plasma electrolysis oxidation cell. In addition, a base layer unit 28 may have dimensions of, for example, 4.5 mm×4.5 mm ($h_2$), whereas the land 30 may have a width of about 1 mm ($h_3$). FIG. 5 describes, as $h_1$, a repeating unit which, as well as the actual base layer unit 28, comprises in each case a half gap on all sides of the base layer unit 28. This size $h_1$ may be about 5 mm, which means that the gap on each side may have, for instance, a thickness of 0.5 mm.

A process according to the invention in this configuration may then proceed as follows. Fixed, for example, in a holder frame, the base layer units 28 can be transported, for instance, by means of a 5-axis movement manipulator into a PEO cell (plasma electrolysis oxidation cell) and be oxidized therein with control of current, voltage and time. In the next process step, the prestructured base layer units 28 are ultrasound-cleaned, in order to remove the adhering electrolyte from the PEO cell. In an oven, the oxidized units are subsequently dried and thermally aftertreated. In the subsequent step, they are transported or manipulated, for example, to a spray-coating cell in which the front electrode or outer layer 18 is produced. The structure of the sensors is then complete. In the plant, it is additionally possible to implement a test device for a sample determination of electrical characteristic data of individual sensor elements or sensors 10. The tester thus serves for a first check of the basic functioning capacity of the sensor elements.

The subsequent individualization of the sensors 10 can be effected by a cutting tool in which the small lateral lands 30 on the finished sensor elements or sensors 10 are severed; these points advantageously become the electrical contacts for subsequent bonding with a conductive silicone adhesive or another conductive adhesive to a header. The header used may be what is called a TO-39 header, which is commercially available for electronic components. The front electrode or outer layer 18 may be bonded in an electrically conductive manner, for instance, via a wire bridge of gold-plated copper to the second insulated contact pin of the header.

The invention claimed is:

1. A sensor having a layer arrangement, wherein the layer arrangement comprises at least a base layer, a middle layer and an outer layer, wherein the middle layer is arranged at least partly upon and in contact with the base layer and wherein the outer layer is arranged at least partly upon and in contact with the middle layer, wherein the base layer comprises a metal, wherein the middle layer comprises a metal oxide, and wherein the outer layer is porous and comprises a material having an open porosity selected from the group comprising electrically conductive carbon compounds and base metals, and wherein electrical contacts can be formed with the base layer and outer layer for a conductivity measurement and/or a resistance measurement, wherein the base layer comprises at least one metal selected from the group comprising titanium, vanadium, chromium, zirconium, niobium, molybdenum, tantalum and tungsten, or an alloy of one or more of these metals with one or more of these or further metals, and wherein the middle layer is a conversion layer of the base layer, said sensor further characterized in that the sensor comprises at least one additive arranged at least partly in the pores of the outer layer.

2. The sensor as claimed in claim 1, wherein said further metals are selected from the group consisting of aluminum, palladium, manganese, iron, nickel, cobalt, copper and rare earth metals.

3. The sensor as claimed in claim 1, characterized in that the outer layer comprises graphite.

4. The sensor as claimed in claim 1, characterized in that the pore width of the outer layer and/or of the middle layer is within a range from ≥10 nm to ≤5000 nm.

5. The sensor as claimed in claim 1, wherein the at least one additive comprises a noble metal such as, more particularly, gold, platinum, palladium, rhodium, iridium, ruthenium or an alloy of one or more of the aforementioned metals.

6. The sensor as claimed in claim 1, characterized in that the at least one additive is arranged on a carrier material, for example on activated carbon, on gamma-alumina or on titanium dioxide.

7. A process for producing a sensor as claimed in claim 1, comprising the process steps of:
 a) providing a base layer, the base layer comprising a metal,
 b) applying a middle layer to at least a portion of the base layer, in such a way that the middle layer is arranged at least partly upon and in contact with the base layer, the middle layer comprising a metal oxide, and
 c) applying an outer layer to at least a portion of the middle layer, in such a way that the outer layer is arranged at least partly upon and in contact with the middle layer, the outer layer being porous and comprising a material selected from the group comprising electrically conductive carbon compounds such as, more particularly, graphite or carbon nanotubes, organic electrical conductors and base metals.

8. The process as claimed in claim 7, comprising the process steps of:
 d) providing an electrolyte;
 e) contacting a base layer with the electrolyte;
 f) contacting an electrode with the electrolyte, wherein
 g) the base layer is connected as the anode and the electrode as the cathode,
 h) applying a voltage between the electrode and the base layer for a predetermined period to form an oxide layer as the middle layer;
 i) removing the base layer together with the middle layer formed in step h) from the electrolyte;
 j) applying an outer layer to at least part of the middle layer.

9. The process as claimed in claim 8, characterized in that the electrolyte used is an alkali or acid, especially an acid, within a concentration range from ≥0.1 mol/liter to ≤16 mol/liter.

10. The process as claimed in claim 8, characterized in that a voltage within a range from ≥50 V to ≤200 V, especially 170 V, is applied.

11. The process as claimed in claim 8, characterized in that the electrolyte is cooled during step h).

12. The process as claimed in claim 7, characterized in that, in step a), a multitude of base layer units secured to one another is provided, and, in steps b) and c), a multitude of sensor units is formed, and the individual sensor units are individualized after process step c), especially by means of a cutting tool.

13. The use of a sensor-as claimed in claim 1 as a gas sensor and/or as a liquid sensor.

\* \* \* \* \*